United States Patent
Burman et al.

(10) Patent No.: US 6,656,970 B2
(45) Date of Patent: Dec. 2, 2003

(54) METHOD AND COMPOSITIONS FOR SOLUBILIZATION OF PENTACYCLIC TRITERPENES

(75) Inventors: Anand C. Burman, Ghaziabad (IN); Rama Mukherjee, Ghaziabad (IN); Honey Bala, Ghaziabad (IN); Dhiraj Khattar, Ghaziabad (IN)

(73) Assignee: Dabur Research Foundation, Uttar Pradesh (IN)

( * ) Notice: Subject to any disclaimer, the term of this patent is extended or adjusted under 35 U.S.C. 154(b) by 121 days.

(21) Appl. No.: 09/802,293

(22) Filed: Mar. 8, 2001

(65) Prior Publication Data

US 2002/0091091 A1 Jul. 11, 2002

(30) Foreign Application Priority Data

May 11, 2000 (IN) ...................... 505/DEL/2000

(51) Int. Cl.$^7$ .................. A61K 31/20; A61K 31/15; A61K 31/21; A61K 31/56
(52) U.S. Cl. .................. 514/569; 514/169; 514/177; 514/178; 514/179; 514/180; 514/181; 514/182
(58) Field of Search ................... 514/569, 169, 514/936, 937, 941, 942, 943

(56) References Cited

U.S. PATENT DOCUMENTS

| | | | | | |
|---|---|---|---|---|---|
| 4,151,273 | A | * | 4/1979 | Riegelman et al. | 424/78 |
| 5,750,578 | A | * | 5/1998 | Carlson et al. | 514/766 |
| 6,124,362 | A | * | 9/2000 | Bradbury et al. | 514/569 |
| 6,172,110 | B1 | * | 1/2001 | Lee et al. | 514/530 |
| 6,214,814 | B1 | * | 4/2001 | Ramadoss et al. | 514/169 |
| 6,217,886 | B1 | * | 4/2001 | Onyuksel et al. | 424/401 |
| 6,228,850 | B1 | * | 5/2001 | Jaggi et al. | 514/169 |

* cited by examiner

Primary Examiner—Zohreh Fay
Assistant Examiner—Brian-Yong S. Kwon
(74) Attorney, Agent, or Firm—Ladas & Parry

(57) ABSTRACT

The present invention provides compositions and methods for the solubilization of poorly soluble drugs such as triterpenes like betulinic acid and/its derivatives in pharmaceutically acceptable liquid vehicles that avoid use of potentially toxic solvents that are often used for the solubilization of poorly soluble drugs. In the compositions of this invention the drugs remain physically and chemically stable and can be administered intravascularly without undue toxicity from undissolved drug and/or from the solvent vehicles at a drug dose meant to be effective to exhibit clinically significant anticancer activity.

9 Claims, No Drawings

METHOD AND COMPOSITIONS FOR SOLUBILIZATION OF PENTACYCLIC TRITERPENES

FIELD OF THE INVENTION

The invention relates to compositions of poorly water-soluble drugs such as triterpenes and methods for preparing the compositions. Particularly, the invention relates to compositions comprising pentacyclic triterpenes and more particularly, betulinic acid and its derivatives. The present invention also relates to betulinic acid and/or its derivatives that are used for the treatment and suppression of malignant diseases including but not limited to leukemias, lymphomas, melanoma, prostate and ovarian cancers.

BACKGROUND OF THE INVENTION

Under the auspices of a National Cooperative Natural Product Drug Discovery Group supported by the National Cancer Institute, the potential anti-tumor activity of approximately 2500 extracts derived from globally collected plants were evaluated in a panel of enzyme based assays and in a battery of cultured human tumor cell lines. One such extract, prepared from the stem bark of *Ziziphus mauritiana Lam.* (Rhamnaceae) displayed selective cytotoxicity against cultured human melanoma cells (Nature Medicine, Vol. 1 (10) 1995, WO 96/29068). As a result of bioactivity guided fractionation, betulinic acid, a pentacyclic triterpene, was identified as a melanoma-specific cytotoxic agent. In follow-up studies conducted with athymic mice carrying human melanomas, tumor growth was completely inhibited without toxicity. As judged by a variety of cellular responses, anti-tumor activity was mediated by the induction of apoptosis.

A number of triterpenoids, including betulinic acid, have several known medical applications, including use as an anticancer drug. Anderson et al., in WO 95/04526, discuss derivatives of triterpenoids which have been used in cancer therapy, including their activity against polyamines which are required by cells to grow at an optimal rate. Some of these triterpenoids have been found to interfere with enzymatic synthesis of polyamines required for optimal cell growth, and thus inhibit the growth of cancer cells, particularly by inhibiting ornithine decarboxylase (Yasukawa, K. et al. Oncology 48:72–76, 1991). The anti-cancer activity of betulinic acid and some derivatives has been demonstrated using mouse sarcoma 180 cells implanted subcutaneously in nude mice (JP 87,301,580). Choi et al have shown that betulinic acid 3-monoacetate, and betulinic acid methyl ester exhibit ED50 values of 10.5 and 6.8 $\mu$g/ml, respectively against P388 lymphocytic leukemia cells (Choi, Y. H. et al. Planta Medica vol. XLVII, pages 511–513, 1988). Betulinic acid and derivatives of betulinic acid have highly selective activity against melanoma cells, murine carcinosarcoma and murine lymphocytic leukemia.

The selective cytotoxicity of betulinic acid and its various derivatives, and their lack of toxicity towards normal cells, afford a favorable therapeutic index. However, the poor solubility of betulinic acid and its derivatives has limited research on other activities of betulinic acid and its derivatives. This is also reflected by the fact that except for a few topical preparations no systemic preparations for the administration of betulinic acid and/or its derivatives are reported. This is due to very poor aqueous solubility of the betulinic acid and its derivatives. To date there is no formulation reported for the administration of these drugs for human use.

There is a need, therefore, for solubilization of betulinic acid and/or its derivatives into pharmaceutically acceptable compositions which are miscible with aqueous intravenous diluting fluids.

It is an important objective of the present invention to solubilize derivatives of betulinic acid and/or its derivatives that have limited utility due to poor solubility.

It is another important objective of the present invention to overcome the poor solubility of the betulinic acid and its derivatives by solubilizing them in a pharmaceutically acceptable non-toxic solvent system.

Another very important objective of the present invention is to provide a pharmaceutically acceptable composition of betulinic acid and its derivatives that can be utilized for the treatment of malignant diseases.

SUMMARY OF THE INVENTION

The present invention aims to overcome the above problems and realize the objects of the present invention by providing a novel, pharmaceutically acceptable solvent system based, inter alia, upon the principles of co-solvency. The solvent system comprises an organic solvent, a co-solvent and a solubilizer.

DETAILED DESCRIPTION OF THE INVENTION

The present invention provides compositions and methods for the solubilization of poorly soluble drugs such as triterpenes like betulinic acid and/its derivatives in pharmaceutically acceptable liquid vehicles that avoid use of potentially toxic solvents that are often used for the solubilization of poorly soluble drugs. In the compositions of this invention the drugs remain physically and chemically stable and can be administered intravascularly without undue toxicity from undissolved drug and/or from the solvent vehicles at a drug dose meant to be effective to exhibit clinically significant anticancer activity. Before intravascular administration, the compositions are diluted in a pharmaceutically acceptable solution that is suitable for intravascular administration.

According to the present invention, a triterpene is dissolved in an organic solvent, followed by the addition of a co-solvent and a solubilizer. Examples of organic solvents that can be used are dimethylacetamide (DMA), dimethylsulphoxide (DMSO), and alcohols such as methanol, ethanol, propanol and isopropanol. Examples of co-solvents that can be used are polyethylene glycol (PEG), ethanol, various amides such as pyrrolidinone or 1-methyl-2-pyrrolidinone, or sulfur containing compounds such as sulfolane, dimethylsulfoxide (DMSO) or tetramethylene sulfoxide. Any other co-solvent that would be suitable for use in this invention can also be used. Preferably, polyethylene glycol (PEG) is used as the co-solvent. The molecular weight of the PEG may vary from about 300 to about 10,000. More preferably the PEG has an average molecular weight of about 300. Examples of solubilizers that can be used include polyoxyethylene sorbitan fatty acid esters, poloxamers, polyoxyethylene stearates or lecithin. A polyoxyethylene sorbitan fatty acid ester such as POLYSORBATE 20, 21, 40, 60, 61, 65, 80, 81, 85 or 120, or TWEEN 80, preferably POLYSORBATE 80 or TWEEN 80, a poloxamer such as a PLURONIC or a polyoxyethylene stearate such as MYRJ 52 can be used as the solubilizer. Any other solubilizer that would be suitable for use in this invention can be used.

According to the invention, betulinic acid or any of its derivatives is dissolved in an organic solvent as the primary vehicle, for example, dimethylacetamide (DMA), followed by the addition of co-solvent(s) such as polyethylene glycol and a solubizer such as polyoxyethylene sorbitan fatty acid ester to retain the drug in solution upon dilution with an aqueous vehicle.

The preferred compositions utilize combinations of anhydrous dimethylacetamide (DMA), as the primary solvent, polyethylene glycol 300 (PEG) as the co-solvent and a polyoxyethylene sorbitan fatty acid ester such as POLYSORBATE 80 as the solubilizer. Such compositions are miscible in solutions that are used in intravenous preparations. These intravenous solutions include but are not limited to solutions that contain 2–25% by weight of dextrose such as 5% dextrose solution, 10% dextrose solution, normal saline or dextrose-normal saline. Any intravenous solution that can be used for humans or animals can be used. These intravenous solutions are examples of vehicles in which betulinic acid or its derivatives are effectively solubilized and can be administered to humans or animals, alone or in combination with other drugs.

Accordingly, the present invention provides a novel pharmaceutical composition for solubilization of triterpenes which comprises from 5% to 50% by volume of an organic solvent, from 20% to 80% by volume of a co-solvent and from 5% to 60% by weight of a solubilizer. Optionally, the composition is diluted with an aqueous intravenous diluting fluid.

In one embodiment of the invention the composition for solubilization of triterpenes comprises from 5–50% of dimethylacetamide (DMA), from 20–80% by volume of polyethylene glycol (PEG) and from 5–60% by weight of polyoxyethylene sorbitan fatty acid ester such as Tween.

In a preferred embodiment, the pharmaceutical composition for solubilization of triterpenes comprises from 20% to 50% by volume of dimethylacetamide (DMA), from 20% to 40% by volume of polyethylene glycol (PEG) and from 5% to 30% by weight of polyoxyethylene sorbitan fatty acid ester such as Tween. Optionally, the composition is diluted with an aqueous intravenous diluting fluid.

In a still more preferred embodiment, the DMA and polyoxyethylene sorbitan fatty acid ester such as TWEEN 80 are present at a ratio of about 1:2 (v/v) and in another preferred embodiment, the DMA and PEG 300 are present at a ratio of about 1:4 (v/v).

It will be understood by a skilled artisan that the present invention will work even outside these ratios.

Preferably the triterpene is betulinic acid

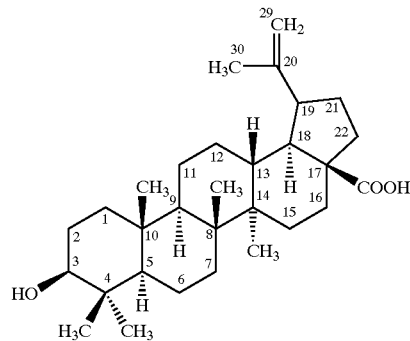

or a derivative thereof.

Given below is the list of some of the representative derivatives of betulinic acid that can be solubilized using the above compositions.

Wherein, Betulinic acid derivatives representing R, $R_1$, $R_2$, $R_3$, and $R_4$ are selected from the following as shown in the Table herein below:

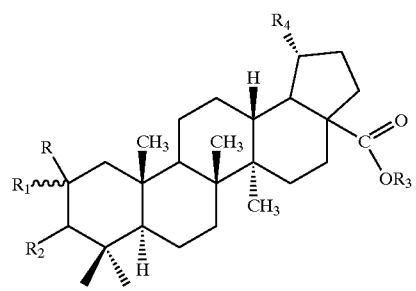

| Derivatives | R | $R_1$ | $R_2$ | $R_3$ | $R_4$ |
|---|---|---|---|---|---|
| MJ-321-RS | H | H | —OCOCH$_3$ | H | CH$_2$=CCH$_3$ |
| MJ-351-RS | H | H | =NOH | H | CH$_2$=CCH$_3$ |
| MJ-353-RS | H | H | =NNHC$_6$H$_5$ | H | CH$_2$=CCH$_3$ |
| MJ-408-RS | H | H | —OCOCH$_3$ | CH$_2$COOCH$_3$ | CH$_2$=CCH$_3$ |
| MJ-481-RS | H | H | =NOCOCH$_3$ | H | CH$_2$=CCH$_3$ |
| MJ-542-RS | H | Br | =O | H | —CH(CH$_3$)$_2$ |
| MJ-606-RS | H | H | —OCOC$_6$H$_5$ | H | —CH(CH$_3$)$_2$ |
| MJ-807-RS | H | H | =NNHCOC$_6$H$_5$ | H | —CH(CH$_3$)$_2$ |
| MJ-912-RS | H | H | —NH NH C$_6$H$_4$OCH$_3$(4) | H | —CH(CH$_3$)$_2$ |
| MJ-939-RS | H | H | —O CO C$_6$H$_4$CF$_3$(3) | H | CH$_2$=C—CH$_3$ |
| MJ-1025-RS | H | H | —NHCOCH$_3$ | —CH$_2$COOCH$_3$ | —CH(CH$_3$)$_2$ |
| MJ-1101-RS | H | H | —OH | —COCH=CH$_2$ | CH$_2$=C—CH$_3$ |
| MJ-1207-RS | H | H | =NNHC$_6$H$_3$Cl$_2$(3,4) | H | CH$_2$=C—CH$_3$ |
| MJ-1305-RS | H | H | —OCOC$_6$H$_4$Cl(4) | H | —CH(CH$_3$)$_2$ |
| MJ-1324-RS | H | H | =NOC$_2$H$_5$ | H | —CH(CH$_3$)$_2$ |
| MJ-1396-RS | H | H | —N[COC$_6$H$_3$F$_2$(2,4)]OCH$_2$C$_6$H$_4$NO$_2$(4) | H | —CH(CH$_3$)$_2$ |
| MJ-1402-RS | H | H | —O Morpholinoyl | H | —CH(CH$_3$)$_2$ |

-continued

| Derivatives | R | $R_1$ | $R_2$ | $R_3$ | $R_4$ |
|---|---|---|---|---|---|
| MJ-1456-RS | H | H | —NHOCH$_2$C$_6$H$_4$[NHCH$_2$C$_6$H$_3$F$_2$(3,4)](4) | H | —CH(CH$_3$)$_2$ |
| MJ-1464-RS | H | Br | =NNHCOC$_6$H$_5$ | H | —CH(CH$_3$)$_2$ |
| MJ-1498-RS | H | H | —NHOCH$_2$C$_6$H$_4$(NHSO$_2$CH$_3$)(4) | Y | —CH(CH$_3$)$_2$ |
| MJ-1529-RS | H | Br | —OCOCH$_3$ | Y | —CH(CH$_3$)$_2$ |
| MJ-1103-RS | H | H | —OH | —COCH=CH$_2$ | —CH(CH$_3$)$_2$ |
| MJ-1104-RS | H | H | —OCOC$_6$H$_4$(C$_5$H$_{11}$)(4) | H | CH$_2$=CCH$_3$ |
| MJ-1602-RS | H | Br | —OH | Y | —CH(CH$_3$)$_2$ |
| MJ-1623-RS | H | H | —OH | —COOH | —COCH$_3$ |
| MJ-548-RS | H | Br | =O | CH$_2$CH$_2$COOCH$_3$ | —CH(CH$_3$)$_2$ |
| MJ-937-RS | H | H | —OCOC$_6$H$_3$F$_2$(2,4) | H | —CH(CH$_3$)$_2$ |
| MJ-998-RS | H | H | —N=CHC$_6$H$_3$F$_2$(3,4) | H | —CH(CH$_3$)$_2$ |
| MJ-1065-RS | H | H | —N=CHC$_6$H$_3$F$_2$(2,4) | H | —CH(CH$_3$)$_2$ |
| MJ-1098-RS | H | H | =NOCH$_2$C$_6$H$_4$NO$_2$(4) | H | —CH(CH$_3$)$_2$ |
| MJ-476-RS | H | H | =O | —COOCH$_2$COOCH$_3$ | —CH(CH$_3$)$_2$ |
| MJ-568-RS | H | H | OH | —COOH | —CH(CH$_3$)$_2$ |
| MJ-456RS | H | H | =O | —COOCH$_2$COOCH$_3$ | —CH$_2$=C—CH$_3$ |

Y = 3-Deoxydihydrobetulinic acid (C$_3$→)

In a preferred embodiment the concentration of triterpene is about 0.001 to 40 mg/ml of the composition before it is diluted with an intravenous solution.

The present invention also provides a method for solubilizing triterpenes which comprises the steps of:

dissolving said triterpene in from 5% to 50% by volume of an organic solvent, from 20% to 80% by volume of a co-solvent and from 5% to 60% by weight of a solubilizer and if desired, diluting said composition with an aqueous intravenous diluting fluid.

The present invention also provides a method for solubilizing triterpenes which comprises the steps of:

dissolving said triterpene in from 5% to 50% by volume of dimethylacetamide (DMA), from 20% to 80% by volume of polyethylene glycol (PEG) and from 5% to 60% by weight of polyoxyethylene sorbitan fatty acid ester and if desired, diluting said composition with an aqueous intravenous diluting fluid.

Preferably, said triterpenes are selected from betulinic acid and its derivatives. More preferably, PEG is added to the solution of betulinic acid or its derivatives at a ratio of DMA:PEG of about 1:4 (v/v), followed by the addition of a polyoxyethylene sorbitan fatty acid ester such as TWEEN 80 at a ratio of DMA: polyoxyethylene sorbitan fatty acid ester of about 1:2 (v/v) to obtain a concentration of betulinic acid or its derivatives of about 0.001 mg/ml to 40 mg/ml. The solution can be diluted to a concentration of triterpene between 0.0001 to less than 40 mg/ml.

The present invention will now be described with reference to the following non-limiting examples.

EXAMPLE 1

Enhanced solubility of betulinic acid in physiologically acceptable solvents.

The solubility of betulinic acid and its derivatives was determined in various individual solvents. Based on the solubility of betulinic acid in these particular vehicles, it was then attempted to enhance the solubility of betulinic acid by mixing different solvents according to the principles of co-solvency (Spiegel and Noseworthy, 1963, Yalkowsky and Roseman, 1981). Different solvent systems were evaluated to arrive at a suitable relevant stock composition. The stock composition would then be diluted with a final solvent or intravenous solution to yield a working formulation of 0.001–40 mg/ml.

EXAMPLE 2

Several methods and compositions were evaluated for their ability to solubilize betulinic acid and its derivatives in water miscible, physiologically acceptable vehicles. The solvents that were tried included DMA, dimethylsulfoxide (DMSO), absolute ethanol, glycerin, polyethylene glycols (PEGs) and propylene glycol, in addition to the aqueous diluting fluids normal saline, and 2–25% dextrose in solution. The solubility's in these solvents is shown in the following table.

| SOLVENT | SOLUBILITY mg/ml |
|---|---|
| N,N Dimethylacetamide (DMA) | ≧200 mg/ml |
| Dimethylsulfoxide (DMSO) | ≦100 mg/ml |
| Polyethylene glycols (MW 200, 300, 400) | <5 mg/ml |
| Absolute ethanol | varies between 3–10 mg/ml depending upon the derivative |
| Glycerin | insoluble |
| Propylene glycol | <5 mg/ml |
| Water | insoluble |

DMA and DMSO were found to be the best solvents, whereas betulinic acid and its derivatives were insoluble in most of the aqueous solvents. Although DMSO has been used as a solvent for parenteral formulations of anti-cancer agents, it is not a preferred vehicle for dissolving drugs due to its toxicity and potential incompatibilities with plastic administration devices. Therefore DMA was chosen as the solvent of choice for dissolving the drug. DMA, per se, could dissolve a concentration of betulinic acid and its derivatives up to 250 mg/ml. However, a concentrated solution of betulinic acid or its derivatives in DMA alone cannot be administered as such in the body as the total volume of the solvent administered in the body would exceed the toxicity limit. Moreover, the solution on dilution with aqueous fluid in the body may lead to precipitation of drug from the solution leading to increased drug toxicity.

The following sets of studies were performed to arrive at physiologically acceptable formulations for intravenous administration.

EXAMPLE 3

Solubilizing of betulinic acid and/or its derivatives using DMA and PEG.

A concentrated solution of betulinic acid or its derivatives was prepared by dissolving 50–200 mg of betulinic acid or its derivatives in 1 ml of DMA. The above stock solution was diluted with PEG (polyethylene glycol, MW 300) in a ratio of 1:4 to a concentration of 10–40 mg/ml.

| Betulinic acid/derivatives | 200 mg |
|---|---|
| DMA | 20% v/v |
| PEG 300 | 80% v/v |

However, on dilution with the aqueous diluting fluid, the drug immediately precipitated out. Therefore, in further trials the drug concentration was reduced.

| Betulinic acid/derivatives | 50 mg |
|---|---|
| DMA | 20% v/v |
| PEG 300 | 80% v/v |

The above solution also on dilution with the aqueous diluting fluid, led to immediate precipitation of drug even at concentrations as low as 0.001–0.1 mg/ml.

Therefore, in further trials an attempt was made to increase the proportion of DMA to enhance the solubility of the drug on dilution.

EXAMPLE 4

| Betulinic acid/derivatives | 50 mg |
|---|---|
| DMA | 50% v/v |
| PEG 300 | 50% v/v |

The 1:1 ratio of DMA and PEG improved the solubility of betulinic acid or its derivatives on dilution with aqueous diluting fluid like 2–25% dextrose, or normal saline. However, 1:1 ratio of DMA and PEG in the presence of betulinic acid or its derivatives and on dilution with aqueous diluting fluid gave a viscous solution which gels over time although there are no signs of any precipitation of drug.

EXAMPLE 5

To further improve the solubility of betulinic acid and its derivatives on dilution with aqueous diluting fluids, additions of surfactants were investigated. The surface-active (solubilizers) agents most commonly used in the prior art for enhancing the solubility of poorly soluble drugs are polyoxyethylene sorbitan monooloeate (Polysorbate 80) and polyoxyethylene polyoxypropylene ethers (Pluronic 68). Less commonly used surface active agents (solubilizers) in parenteral products are lecithins, Polyoxyl 40 stearate (MYRJ 52).

In the following examples one or more co-solvents with a solubilizers or a combination of (solubilizers) was added to keep the drug in solution after diluting with an aqueous intravenous diluting fluid.

EXAMPLE 6

| Betulinic acid/derivatives | 10–20 mg |
|---|---|
| DMA | 50% v/v |
| Tween 80 | 50% w/v |

The above combination could dissolve upto 20 mg/ml of the drug. However, the drug immediately precipitated out on dilution with aqueous diluting fluid.

EXAMPLE 7

| Betulinic acid/derivatives | 10–20 mg |
|---|---|
| Absolute ethanol | 20-40% v/v |
| Tween 80 | 60-80% w/v |

The above composition could dissolve upto 20 mg/ml of the drug. However, the drug solution only remained clear for a maximum of 3 hours on dilution with aqueous diluting fluid to a concentration of 0.3–1.4 mg/ml.

EXAMPLE 8

| Betulinic acid/derivatives | 60 mg |
|---|---|
| Absolute ethanol | 65% v/v |
| Tween 80 | 5% w/v |
| PEG 300 | 30% v/v |

The above composition could dissolve up to 6 mg/ml of the drug. The drug solution remained clear on dilution with aqueous diluting fluid to a concentration of 0.08–0.4 mg/ml.

EXAMPLE 9

In this experiment, the amount of the organic solvent was reduced.

| Betulinic acid/derivatives | 40 mg |
|---|---|
| Absolute ethanol | 35% v/v |
| Tween 80 | 15% w/v |
| PEG 300 | 50% v/v. |

The above composition could dissolve only up to 4 mg/ml of the drug. The drug solution remained clear on dilution with aqueous diluting fluid to a concentration of 0.08 to 0.4 mg/ml. However, outside this range there was immediate precipitation.

EXAMPLE 10

| Betulinic acid/derivatives | 150 mg |
|---|---|
| DMA | 20% v/v |
| Propylene glycol | 10% v/v |
| Absolute ethanol | 30% v/v |
| Tween 80 | 40% w/v |

EXAMPLE 11

| Betulinic acid/derivatives | 30 mg |
|---|---|
| DMA | 10% v/v |
| Propylene glycol | 20% v/v |
| Absolute ethanol | 35% v/v |
| Tween 80 | 35% w/v |

Betulinic acid and almost all of its derivatives were found to be soluble in the above system in a concentration range of 2–15 mg/ml which on dilution with an aqueous diluting fluid remains clear at a lower concentration of 0.012–2 mg/ml. However, these compositions had a quite high amount of the organic solvents which is not desirable as these may prove toxic on administration in the body. Therefore, attempts were undertaken to solubize the maximum quantity of the drug in a minimum amount of the organic solvents with a less toxic co-solvent and surfactant combination.

EXAMPLE 12

| Betulinic acid/derivatives | 5–20 mg/ml |
|---|---|
| DMA | 20% v/v |
| MYRJ 52 | 30% w/v |
| Tween | 50% w/v |

EXAMPLE 13

| Betulinic acid/derivatives | 5–20 mg/ml |
|---|---|
| DMA | 20% v/v |
| MYRJ 52 | 20% w/v |
| Tween 80 | 20% w/v |
| PEG 300 | 40% v/v |

The above two compositions containing MYRJ 52 could dissolve upto 20 mg/ml of the drug but on dilution with aqueous diluting fluid to a concentration to 0.1–1.0 mg/ml, the drug precipitated out in a few hours. Moreover, preparations containing MYRJ 52 tend to solidify at lower temperatures. Also MYRJ 52 is not a preferred solubilizing agent for parenteral products because of its higher toxicity. Therefore it was attempted to replace MYRJ 52 with Pluronic 68 and lecithin, which are comparatively safer for intravenous administration.

EXAMPLE 14

| Betulinic acid/derivatives | 2–15 mg/ml |
|---|---|
| DMA | 20% v/v |
| Tween 80 | 20% w/v |
| PEG 300 | 57% v/v |
| Poloxamer 407 | 3% w/v |

EXAMPLE 15

| Betulinic acid/derivatives | 2–15 mg/ml |
|---|---|
| DMA | 20% v/v |
| Tween 80 | 20% w/v |
| Lecithin | 5% w/v |
| PEG 300 | 55% v/v |

The above compositions could dissolve 2–15 mg/ml of betulinic acid and its derivatives. However, on dilution with the aqueous diluting fluid the drug remained soluble only at lower dilutions (0.001–1 mg/ml).

EXAMPLE 16

After conducting a number of trials as described above to solubilize betulinic acid and its derivatives the most preferred composition was the one containing DMA, PEG 300 and Tween 80. The three components were tried in varying proportions as mentioned in the following example. Up to 22 mg/ml of betulinic acid and/or its derivatives could be dissolved in these compositions. On dilution with an aqueous diluting fluid to a concentration of 0.1–10 mg/ml the composition remained clear for more than 5 days without any precipitation of the drug.

| Betulinic acid/derivative | 10–20 mg/ml |
|---|---|
| DMA | 20–50% v/v |
| PEG 300 | 20–40% v/v |
| Tween 80 | 5–30% w/v |

What is claimed is:

1. A composition comprising up to 22 mg/ml of a triterpene, from 20% to 50% by volume of dimethylacetamide; from 20% to 40% by volume of polyethylene glycol and from 5% to 30% by weight of polyoxethylene sorbitan fatty acid ester.

2. The composition according to claim 1, wherein the triterpene is betulinic acid or a derivative thereof.

3. The composition according to claim 1, wherein the polyethylene glycol has a molecular weight of 300–10,000.

4. The composition according to claim 1, further comprising an aqueous diluting fluid.

5. The composition according to claim 4, wherein the aqueous diluting fluid is selected from 5% dextrose solution, 10% dextrose solution, normal saline, or dextrose-normal saline.

6. A method for increasing the solubility of a triterpene which comprises:

dissolving the triterpene in from 5% to 50% by volume of an organic solvent selected from the group consisting of dimethylacetamide, dimethysulphoxide and alcohols; from 20% to 80% by volume of a co-solvent selected from the group consisting of polyethylene glycol, ethanol, an amide, sulfolane, dimethysulfoxide and tetramethylene sulfoxide and from 5% to 60% by weight of a solubilizer selected from the group consisting of polyoxyethylene sorbitan fatty acid ester, poloxamer, polyoxyethylene stearates and lecithin.

7. The method according to claim 6, further comprising adding a diluting fluid.

8. The method according to claim 6, wherein the solvent is dimethylacetamide, the co-solvent is polyethylene glycol and the solubilizer is polyoxyethylene sorbitan fatty acid ester.

9. The method according to claim 8, further comprising adding a diluting fluid.

* * * * *